United States Patent [19]

Okabe et al.

[11] Patent Number: 4,769,184

[45] Date of Patent: Sep. 6, 1988

[54] PROCESS FOR PRODUCING CARBONYL FLUORIDE COMPOUND

[75] Inventors: Jun Okabe, Kitaibaraki; Haruyoshi Tatsu, Hitachi, both of Japan

[73] Assignee: Nippon Mektron Limited, Tokyo, Japan

[21] Appl. No.: 121,135

[22] Filed: Nov. 16, 1987

[30] Foreign Application Priority Data

Sep. 8, 1987 [JP] Japan ............................ 62-222946
Oct. 2, 1987 [JP] Japan ............................ 62-249588

[51] Int. Cl.$^4$ ............................................ C07L 51/04
[52] U.S. Cl. .................................................. 260/544 F
[58] Field of Search ..................................... 260/544 F

[56] References Cited

U.S. PATENT DOCUMENTS

| | | | |
|---|---|---|---|
| 3,125,599 | 3/1964 | Warnell | 260/544 F |
| 3,451,908 | 6/1969 | Sianesi | 260/544 F |
| 3,637,842 | 1/1972 | Paine | 260/544 F |
| 3,665,041 | 5/1972 | Sianesi et al. | 260/544 F |
| 3,715,378 | 2/1973 | Sianesi et al. | 260/544 F |

FOREIGN PATENT DOCUMENTS 725740  1/1966  Canada ............................ 260/544 F

*Primary Examiner*—Paul J. Killos
*Attorney, Agent, or Firm*—Fred Philpitt

[57] ABSTRACT

A useful carbonyl compound as an intermediate for producing perfluoro(lower alkyl vinyl ether) can be obtained by thermally decomposing a polyether compounds represented by the following general formulas at a temperature of about 180° C.–about 400° C. in the presence of an activated carbon catalyst:

$$RfO(CF_2CF_2O)_a (CF_2O)_b (O)_c Rf',$$

or $$RfO(CFXCF_2O)_n CFX'Y$$

6 Claims, No Drawings

PROCESS FOR PRODUCING CARBONYL FLUORIDE COMPOUND

BACKGROUND OF THE INVENTION

1. Field of the Invention

This invention relates to a process for producing a carbonyl fluoride compound, and more particularly to a process for producing a carbonyl fluoride compound useful as an intermediate for producing perfluoro (lower alkyl vinyl ethers).

2. Description of the Prior Art

Perfluoro (lower alkyl vinyl ethers), for example, perfluoro (propyl vinyl ether), perfluoro (ethyl vinyl ether), perfluoro (methyl vinyl ether), etc. are important compounds as raw material monomers for producing fluorine-containing resin, fluorine-containing rubber, etc.

These perfluoro (lower alkyl vinyl ethers) are prepared by addition reaction between a carbonyl fluoride compound such as perfluoroacetyl fluoride ($CF_3COF$), carbonyl fluoride ($COF_2$), etc. as a raw material and perfluoroalkene oxide and successively $COF_2$-releasing reaction (U.S. Pat. No. 3,291,843).

For example,

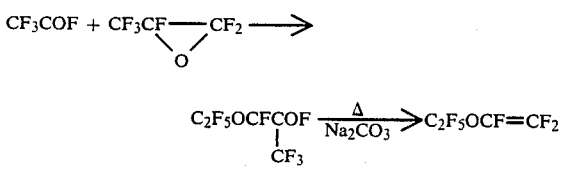

CF₃COF used as a raw material for the reaction has been so far synthesized by reaction of trichloroacetyl chloride ($CCl_3COCl$) with hydrogen fluoride and successibe halogen exchange (Chemical Abstract, Vol. 78, 42856z). However, the product $CF_3COF$ contains chlorine as an impurity and when the product $CF_3COF$ is used in the above-mentioned reaction as the raw material, there is a high possibility that the desired product perfluoro (alkyl vinyl ether) contains chlorine-based impurities.

$COF_2$ likewise used in the above-mentioned reaction as the raw material is generally prepared by halogen exchange reaction between phosgene ($COCl_2$) and a metal fluoride (CHEMISTRY OF ORGANIC FLUORINE COMPOUNDS, 2nd Ed. page 678, 1976). Phosgene is highly toxic and contains unwanted COClF as an impurity. Thus, $COF_2$ of high purity cannot be obtained from such a raw material phosgene.

Furthermore, perfluoro (propyl vinyl ether) has been so far prepared by oligomerization of hexafluoropropylene oxide as a raw material (U.S. Pat. Nos. 3,250,807 and 3,250,808). In the oligomerization reaction, only the desired 2-(heptafluoropropoxy) propionyl fluoride is not selectively formed, but polyether compounds having a high degree of polymerization [n is 1 or higher in the general formula (XII) which will be given later] are by-produced at the same time. This is a problem.

Hexafluoropropylene oxide used in the oligomerization reaction as the raw material is an expensive compound, and the by-production of the polyether compounds having a high degree of polymerization will lower the yield of the desired product, increasing its cost. Though the trimer and tetramer (n=1-2) among the by-products can be used as surfactants, the pentamer or higher obigomers (n=3 or higher) has no special application. This is another problem.

The present inventors have made extensive studies to find a process for producing a carbonyl fluoride compound containing no chlorine-based impurities in the process for producing perfluoroacetyl fluoride from the trichloroacetyl chloride and the process for producing carbonyl fluoride from the phosgene, and have found that the problem can be effectively solved by thermal decomposition of a polyether compound obtained by reaction of tetrafluoroethylene with oxygen under irradiation of ultraviolet rays.

Furthermore, the present inventors have made extensive studies to produce perfluoropropionyl fluoride as a useful compound from oligomers such as trimer and higher oligomers of hexafluoropropylene oxide by-produced when perfluoro (propyl vinyl ether) is produced from hexafluoropropylene oxide, and have found that the problem can be effectively solved by thermal decomposition of the oligomers in the presence of an activated carbon catalyst. Furthermore, the present inventors have found that the thermal decomposition process can be effectively applied not only to the hexafluoropropylene oxide oligomers, but also to tetrafluoroethylene oxide oligomers.

SUMMARY OF THE INVENTION

An object of the present invention is to provide a process for producing perfluoroacetyl fluoride or carbonyl fluoride containing no chlorine-based impurities.

Another object of the present invention is to provide a process for producing useful perfluoropropionyl fluoride or perfluoroacetyl fluoride from useless oligomers by-produced when perfluoro(lower alkyl vinyl ethers) is produced from hexafluoropropylene oxide or tetrafluoroethylene oxide.

DETAILED DESCRIPTION OF THE PREFERRED EMBODIMENTS

These carbonyl fluoride compounds are prepared according to any of the following processes.

[A] process for producing a carbonyl fluoride compound represented by the following general formula [I]:

$$XCOF \qquad [I]$$

where X is a fluorine atom or $-CF_3$.

process for thermal decomposition of a polyether compound represented by the following general formula [II] at a temperature of about 180°–about 400° C. in the presence of an activated carbon catalyst:

where Rf is a perfluoro-lower alkyl group; Rf′ is $-COF$ or $-CF_3$; the $CF_2CF_2O$ groups, the $CF_2O$ groups and the O groups are destributed at random; a and b are not O, c can be O, a+b+c is a value not more than about 200, preferably not more than 40.

It is known that the polyether compound represented by the foregoing general formula [II] can be obtained by reaction of tetrafluoroethylene with oxygen under irradiation of ultraviolet rays (for example, see Japanese Patent Publications Nos. 49-45719 and 55-50052).

As a result of the reaction, a peroxide bond-containing acid fluoride compound given by the following general formula [III] is generally obtained at first:

The peroxide bond is removed therefrom by heating the acid fluoride compound [III] at a temperature of about 50°–about 400° C. in a nitrogen gas stream to obtain an acid fluoride compound given by the following general formula [IV]:

$$R_fO(CF_2CF_2O)_{a'}(CF_2O)_{b'}COF \qquad [IV]$$

Then, the acid fluoride compound [IV] is treated with a fluorine gas, generally a nitrogen-diluted fluorine gas at a temperature of about 100°–about 300° C., whereby it is converted to a perfluoropolyether compound given by the following general formula [V]:

$$R_fO(CF_2CF_2O)_{a''}(CF_2O)_{b''}CF_3 \qquad [V]$$

In the present process, any of these compounds [II]–[V] can be used as a raw material, and thus a and b are not 0, and c can be 0. A value of $a+b+c$ is generally not more than about 200 from the viewpoint of easiness in their production.

[B] Process for producing a carbonyl fluoride compound represented by the following general formula [XI]:

$$CF_2XCOF \qquad [XI]$$

where X is a fluorine atom or —$CF_3$:

Process for thermal decomposition of a polyether compound represented by the following general formula [XII] at a temperature of about 180°–about 400° C. in the presence of an activated carbon catalyst:

$$R_fO(CFXCF_2O)_nCFX'Y \qquad [XII]$$

where Rf is a perfluoro-lower alkyl group; X has the same meaning as defined above; X' is —$CF_3$, a fluorine atom or a hydrogen atom; Y is —COF, —COOH, —COOR or —$CF_3$; R is a lower alkyl group; and n is 1–50, preferably 1–about 10.

As the polyether compound represented by the foregoing general formula [XII], the following compounds can be used, depending upon the species of the X' group and Y group, $$R_fO(CFXCF_2O)_nCFXCOF \qquad [XIII]$$

$$R_fO(CFXCF_2O)_nCFXCOOH \qquad [XIV]$$

$$R_fO(CFXCF_2O)_nCFXCOOR \qquad [XV]$$

$$R_fO(CFXCF_2O)_nCF_2X \qquad [XVI]$$

$$R_fO(CFXCF_2O)_nCFHX \qquad [XVII]$$

The acid fluoride compound represented by the foregoing general formula [XIII] can be obtained according to processes disclosed in U.S. Pat. Nos. 3,250,807 and 3,250,808, that is, by subjecting hexafluoropropylene oxide or tetrafluoroethylene oxide to anionic polymerization in the presence of a cesium fluoride catalyst.

The carboxylic acid compound represented by the foregoing general formula [XIV] can be obtained according to processes disclosed in Japanese Patent Publications Nos. 38-12197 and 62-10490, that is, by contacting an acid fluoride compound [XIII] as such or in a solution of a fluorohydrocarbon solvent such as perfluoro (dimethyl cyclobutane), trifluorotrichloroethane, etc. with water at room temperature.

The ester compound represented by the foregoing general formula [XV] can be obtained by subjecting an acid fluoride compound [XIII] to esterification reaction with an alcohol such as methanol, ethanol, propanol, butanol, etc. The esterification reaction can be carried out even at room temperature by mixing the acid fluoride compound [XIII] with a large excess of the dehydrated alcohol.

The perfluoropolyether compound represented by the foregoing general formula [XVI] can be obtained according to a process disclosed in Japanese Patent Publication No. 62-10490, that is, by treating an acid fluoride compound [XIII] with a fluorine gas at a temperature of about 100°–about 350° C.

The polyether compound represented by the foregoing general formula [XVII] can be obtained by mixing an acid fluoride compound [XIII] with triethanolamine, a triethylamine-water mixture, or a dimethylformamide-water mixture and subjecting the resulting mixture to reaction at a temperature of about 150°–about 250° C.

As the terminal group Y, an amido group, a cyano group, a hydroxyalkyl group, a chlorine atom, a bromine atom, an iodine atom, etc. can be used in addition to the foregoing groups.

Thermal decomposition of any of the foregoing polyether compounds as the raw material is carried out at a temperature of about 180°–about 400° C. in the presence of an activated carbon catalyst.

The activated carbon for use as the catalyst can be in any form such as a powdery form, a granular form, a honeycomb form, a rod form, a cylindrical form, etc. and it is desirable to use an activated carbon catalyst having a surface area of particularly about 1–about 300 $m^2/g$, preferably about 20–about 200 $m^2/g$. It is also about 200°–about 600° C. in a dried nitrogen gas stream, because the side reaction by the adsorbed moisture can be suppressed.

The reaction using such an activated carbon catalyst is carried out at a temperature of about 180°–about 400° C., preferably about 280°–about 340° C. A lower temperature than about 180° C., is not preferable from the viewpoint of economy and efficiency, because the thermal decomposition rate is too low, whereas a higher temperature than about 400° C. is also not preferable, because of a higher energy cost and accelerated deterioration of the reactor materials.

The thermal decomposition reaction is carried out under the atmospheric pressure or a superatmospheric pressure, and generally in the atmospheric pressure. The form of reaction can be either gaseous phase reaction or liquid phase reaction, and generally a gaseous reaction system where the raw materials vaporized by preheating at an appropriate temperature is brought into contact with the catalyst is preferable. For the gaseous phase reaction, any reaction system such as a fixed bed, a fluidized bed, a moving bed, etc. can be used. Specifically, a polyether compound as the raw material is trickled into a preheated vaporization chamber maintained at a temperature of about 100°–about 300° C., and entrained into a helium gas passing through the preheated vaporization chamber, whereby the vaporized polyether compound entrained in the helium gas is led to a reactor tube filled with the activated carbon catalyst and subjected to thermal decomposition.

In carrying out the reaction, the raw material entrained in the carrier gas such as the helium gas, etc. is brought, as such, into contact with the activated carbon catalyst, or, if necessary, the raw material as a solution in a perfluorohydrocarbon solvent such as perfluorocyclohexane, perfluoroisohexane, perfluoroisononane, etc. can be brought into the contact with the catalyst. It is desirable that a flow velocity of the fluid passing through the catalyst bed, $SV(hr^{-1})$, that is, the contact time of the raw material with the catalyst, is about 5–about 1,000, preferably about 50–about 300.

After the end of reaction, the reaction mixture is passed through necessary traps selected successively from an ice trap, a dry ice-methanol trap and a liquefied nitrogen trap, and the components trapped therein are subjected to a low temperature distillation, whereby the desired reaction product is separated therefrom.

The carbonyl fluoride compounds obtained according to the present invention are perfluoroacetyl fluoride where X is $-CF_3$ or carbonyl fluoride where X is a fluorine atom in the general formula [I], and perfluoropropionyl fluoride where X is $-CF_3$ or perfluoroacetyl fluoride where X is fluorine atom in the general formula [XI]. These reaction products have been confirmed by infrared absorption spectrum and $^{19}F$-NMR spectrum.

|  | Infrared absorption spectrum: |
|---|---|
| —COF | $1890 \text{ cm}^{-1}$ |
| $^{19}F$-NMR spectrum ($CF_3COOH$ external standard): | |
| $COF_2$ | −48 ppm |
| $CF_3COF$ | −85 ppm +3 ppm |
| $CF_3CF_2COF$ | −94 ppm +11 ppm +48 ppm |

Important carbonyl fluoride compounds as raw materials for the synthesis of perfluoro (lower alkyl vinyl ethers) according to the present invention can be obtained (A) as compounds containing no harmful impurities by thermal decomposing polyether compounds obtained by reaction of tetrafluoroethylene with oxygen under irradiation of ultraviolet rays, or (B) as useful compounds from useless oligomers by thermally decomposing oligomers by-produced when the perfluoro (lower alkyl vinyl ethers) are produced by oligomerizing hexafluoropropylene oxide or tetrafluoroethylene oxide.

The polyether compound as the raw material of the latter procedure, where n is about 10 in the general formula [XII], is used as a vacuum pump oil for the production of semiconductors, and is liable to contain various terminal groups (the Y group in the general formula [XII]) owing to the regeneration of the used vacuum pump oil. The present invention can be effectively applied to such a mixture to efficiently obtain perfluorocarboxyl fluorides.

The present invention will be described in detail below, referring to Examples.

REFERENCE EXAMPLE 1

According to the process disclosed in Japanese Patent Application No. 49-45719, 2 l/min. of tetrafluoroethylene and 5 l/min. of oxygen were supplied to a reactor under irradiation of rating 400 W ultraviolet rays, using trifluorotrichloroethane as a solvent, while maintaining the reaction temperature at $-13°\pm5°$ C. and polymerization reaction was carried out for 2 hours 40 minutes. Then, the supply of the reactant gases were discontinued, but the irradiation onto the liquid phase was continued for further 12 hours.

After the end of the reaction, the solvent was removed therefrom by distillation, whereby 77 g oily matters (kinematic viscosity at 40° C.: 13 cst) was obtained. The oily matters were determined to be a peroxide bond-containing acid fluoride compound having the following structure by F-NMR spectrum analysis and infrared absorption spectrum analysis.

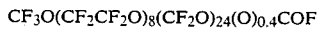

$$CF_3O(CF_2CF_2O)_8(CF_2O)_{24}(O)_{0.4}COF \qquad [VI]$$

REFERENCE EXAMPLE 2

The peroxide bond-containing acid fluoride compound [VI] obtained in Reference Example 1 was charged into a glass reactor and slowly heated to 180° C. in a nitrogen gas stream and then kept 180° C. for 10 hours. A small amount of sample was taken out of the reactor and subjected to F-NMR spectrum analysis and infrared absorption spectrum analysis, and it was found that the compound [VI] was converted to a peroxide bond-free acid fluoride compound having the following structure (kinematic viscosity at 40° C.:8 cst):

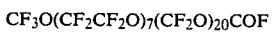

$$CF_3O(CF_2CF_2O)_7(CF_2O)_{20}COF \qquad [VII]$$

REFERENCE EXAMPLE 3

The acid fluoride compound [VII] obtained in Reference Example 2 was maintained in the glass reactor at 180° C., while the gas stream to the reactor was changed from the nitrogen gas to a fluorine gas diluted to 20% with a nitrogen gas, and subjected to fluorination treatment while maintaining 180° C. for further 8 hours, whereby 7.7 l of fluorine gas was consumed.

After the end of reaction, the reaction mixture was distilled at 250° C. under 0.1 Torr to remove all the distillates, whereby 28 g of oily residues (kinematic viscosity at 40° C.:12 cst) was obtained. It was found by F-NMR spectrum analysis and infrared absorption spectrum analysis that the oily residues are a perfluoropolyether compound having the following structure:

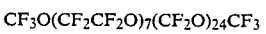

$$CF_3O(CF_2CF_2O)_7(CF_2O)_{24}CF_3 \qquad [VIII]$$

EXAMPLE 1

100 g of granular activated carbon was filled into a stainless steel reactor tube, ½ inch in diameter, in an electric furnace, and the filled granular activated carbon was heated at 400° C. by the electric furnace and pretreated by passing 100 ml/min. of a dried nitrogen gas stream for 14 hours. The pretreated granular activated carbon was used for reaction.

100 g of the acid fluoride compound [VI] obtained in Reference Example 1 was trickled into a preheated vaporization chamber maintained at 200° C. at a trickling rate of about 1.7 g/min., entrained into 75 ml/min. of a helium gas stream passing through the preheated vaporization chamber, fed to the reactor tube filled with the granular activated carbon heated at 300° C. and subjected to thermal decomposition.

The gaseous reaction mixture was successively passed through an ice trap, a dry ice-methanol trap and a liquefied nitrogen trap provided downstream of the thermal decomposition column to trap the product. As a result, 15 g of the product was trapped in the dry ice-methanol trap and 52 g of the product was trapped in the liquefied nitrogen trap.

It was identified by gas chromatography, infrared absorption spectrum analysis and F-NMR analysis that the main component of the trapped products was carbonyl fluoride. Separation of COF$_2$ from CF$_3$COF was carried out by low temperature distillation.

| Gas chromatography: | |
|---|---|
| COF$_2$ | 78.2% |
| CF$_3$COF | 21.8% |

EXAMPLES 2-3

In place of the acid fluoride compound [VI], the same amount of the acid fluoride compound [VII] or perfluoropolyether compound [VIII] was used in Example 1.

The amounts of the trapped products and gas chromatography are as follows:

| | Example 2 | Example 3 |
|---|---|---|
| Product trapped in dry ice-methanol trap (g) | 18 | 16 |
| product trapped in liquefied nitrogen trap (g) | 47 | 55 |
| COF$_2$ (%) | 70.7 | 74.6 |
| CF$_3$COF (%) | 29.3 | 25.4 |

REFERENCE EXAMPLE 4

According to the process disclosed in U.S. Pat. No. 3,250,808, 2 kg of hexafluoropropylene oxide was polymerized at −30° C. in the presence of 15 g of cesium fluoride as a catalyst and 22 g of tetraethyleneglycol dimethyl ether as a solvent.

The resulting reaction mixture was heated to separate tetraethyleneglycol dimethyl ether therefrom, and then the precipitated cesium fluoride was removed therefrom by filtration. Then, the residues were distilled at 360° C. under 1 Torr to obtain 200 g of distillate. It was found by F-NMR spectrum analysis and infrared absorption spectrum analysis that the distillate was an acid fluoride compound having the following structure:

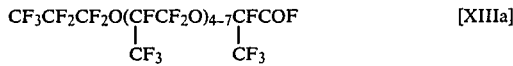  [XIIIa]

REFERENCE EXAMPLE 5

To the acid fluoride compound [XIIIa] obtained in Reference Example 4 was added 10-fold amount of trifluorotrichloroethane. Then, the same volume of water as that of the solvent was added to the solution to conduct hydrolysis reaction of the acid fluoride compound, and the following corresponding carboxylic acid compound was obtained. The hydrolysis reaction was carried out at room temperature for 6 hours, and then the solvent and water were removed from the reaction mixture by distillation, and then distillates at 100° C. under 1 Torr were removed therefrom.

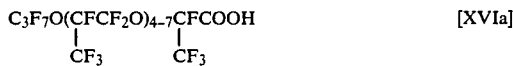  [XVIa]

REFERENCE EXAMPLE 6

The acid fluoride compound [XIIIa] obtained in Reference Example 4 was subjected to reaction with a large excess of dehydrated ethanol at room temperature for 15 hours. The resulting reaction product was washed with water and dried, whereby the following corresponding ester compound was obtained:

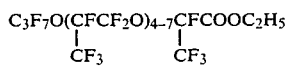  [XVa]

REFERENCE EXAMPLE 7

In the distillation of Reference Example 4, all distillates were removed from the residues, whereby 1.6 kg of liquid residues (kinematic viscosity at 40° C.:408 cst) was obtained (yield: 80%).

It was found by F-NMR spectrum analysis and infrared absorption spectrum that the liquid residues were an acid fluoride compound having the following structure:

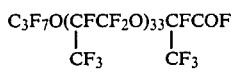  [XIIIb]

REFERENCE EXAMPLE 8

The acid fluoride compound [XIIIb] obtained in Reference Example 7 was charged into a glass reactor and treated with a fluorine gas diluted to 20% with a nitrogen gas at 300° C. for 4 hours, whereby 12.3 l of the fluorine gas on the basis of 25° C. and 1 atom (this basis will be hereinafter used) and 1.57 kg of perfluoropolyether compound having the following structure (kinematic viscosity at 40° C.:397 cst) was obtained (yield: 78%).

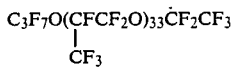  [XVIa]

REFERENCE EXAMPLE 9

In Reference Example 4, fractions at 180°-280° C. under 0.1-3 Torr (kinematic viscosity at 40° C.:17 cst) were obtained from the distillates at 360° C. under 1 Torr and was found by F-NMR analysis to be an acid fluoride compound having the following structure:

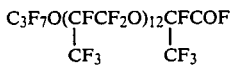  [XIIIc]

To 50 g of the acid fluoride compound was added 50 g of triethanolamine, and the resulting mixture was subjected to reaction at 250° C. for 8 hours. The reaction mixture was washed with water and then the underlayer was recovered therefrom and again distilled, whereby 37 g of fraction was obtained at 180°-280° C. under 0.5-5 Torr. The fraction was found by infrared absorption spectrum to be a polyether compound having the following structure:

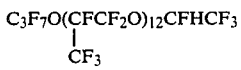  [XVIIa]

REFERENCE EXAMPLE 10

According to the process disclosed in U.S. Pat. No. 3,250,808, 55 g of tetrafluoroethylene oxide was polymerized at a temperature of −78° to −45° C. in the presence of 1 g of activated carbon as a catalyst for 25 hours. The resulting reaction mixture was dissolved in perfluoro(dimethylcyclobutane) and the solution was filtered, whereby a white, waxy matter was obtained. The white, waxy matter was distilled at 300° C. or higher under 0.1 Torr to remove all the distillates therefrom, whereby wax residues at the ordinary temperature (fluid at an elevated temperature) were obtained. The residues were found by F-NMR spectrum analysis and infrared absorption spectrum analysis to be an acid fluoride compound having the following structure:

$$CF_3CF_2O(CF_2CF_2O)_{22}CF_2COF \quad [XIIId]$$

REFERENCE EXAMPLE 11

According to the process disclosed in U.S. Pat. No. 3,250,808, 2 kg of hexafluoropropylene oxide was polymerized at +30° C. in the presence of 15 g of cesium fluoride as a catalyst and 22 g of tetraethyleneglycol dimethl ether as a solvent for 4 hours.

The resulting reaction mixture was heated to separate tetraethyleneglycol dimethyl ether therefrom, and then the precipitated cesium fluoride was removed therefrom by filtration. Then, the residues were distilled, whereby 1,820 g of distillates having the following structure was obtained. It was found by F-NMR spectrum analysis and infrared absorption spectrum analysis that these distillates were an acid fluoride compound having the following structure:

| $CF_3CF_2CF_2O(CFCF_2O)_n CFCOF$ <br>                                  $CF_3$       $CF_3$ | [XIIIe] |
|---|---|
| n = 0   fraction at a boiling point of 56° C. | 579 g |
| n = 1   fraction at a boiling point of 108°–110° C. | 617 g |
| n = 2   fraction at a boiling point of 163°–167° C. | 462 g |
| n = 4   fraction at a boiling point of 126°–131° C./ 80 mmHg | 162 g |

EXAMPLE 4

100 g of granular activated carbon was filled into a stainless steel reactor tube, ½ inch in diameter, in an electric furnace, and the filled granular activated carbon was heated to 400° C. by the electric furnace and pretreated with 100 ml/min. of a dried nitrogen gas stream for 14 hours. The pretreated granular activated carbon was used for reaction.

300 g of the acid fluoride compound [XIIIa] obtained in Reference Example 4 was trickled into a preheated vaporization chamber maintained at 200° C. at a trickling rate of about 1.7 g/min., entrained into 75 ml/min. of a helium gas stream passing through the preheated vaporization chamber, fed to the reactor tube filled with the granular activated carbon and heated at 300° C., and subjected to thermal decomposition.

The resulting gaseous reaction mixture was successively passed through an ice trap, a dry ice-methanol trap and a liquefied nitrogen trap provided downstream of the thermal decomposition column to trap the product. In the dry ice-methanol trap, 268 g of a colorless, transparent liquid product (gas at the ordinary temperature) was obtained.

The main component of the liquid product was identified by gas chromatography, infrared absorption spectrum analysis and F-NMR spectrum analysis to be perfluoropropionyl fluoride.

| Gas chromatography: | |
|---|---|
| $CF_3CF_2COF$ | 87.3% |
| $CF_3COF$ | 6.9% |
| $COF_2$ | 5.7% |

EXAMPLES 5–6

In Example 4, the carboxylic acid compound [XIVa] obtained in Reference Example 5 or the ester compound [XVa] obtained in Reference Example 6 was used in place of the acid fluoride compound [XIIIa], whereby 229 g or 231 g, respectively, of the product trapped in the dry ice-methanol trap was obtained. These products trapped in the dry ice-methanol trap were analyzed in the same manner as in Example 4 and found to have the same result as in Example 4.

EXAMPLE 7

In Example 4, the acid fluoride compound [XIIIb] of Reference Example 7 was used in place of the acid fluoride compound [XIIIa] and the trickling rate was changed to 5.0/min. As a result of the reaction, 187 g of a liquid product (kinematic viscosity at 40° C.:10 cst) was obtained in the ice trap provided downstream of the thermal decomposition column, and 97 g of the product (gas at the ordinary temperature) was obtained in the dry ice-methanol trap.

Gas chromatography of the product trapped in the dry ice-methanol trap:

| $CF_3CF_2COF$ | 97.8% |
|---|---|
| $CF_3COF$ | 1.0% |
| $COF_2$ | 1.2% |

EXAMPLE 8

In Example 7, the trickling rate of the acid fluoride compound was changed to 1.0 g/min., the helium gas flow rate to 25 ml/min., and the reactor tube temperature to 280° C. As a result of the reaction, 275 g of the product was obtained in the dry ice-methanol trap.

EXAMPLE 9

In Example 8, the reactor tube temperature was changed to 250° C., whereby 17 g of the liquid product was obtained in the ice trap and 239 g of the product was obtained in the dry ice-methanol trap.

EXAMPLE 10

In Example 8, the trickling rate of the acid fluoride compound was changed to 0.5 g/min., and the reactor tube temperature to 230° C., whereby 16 g of the liquid product was obtained in the ice trap and 241 g of the product was obtained in the dry ice-methanol trap.

EXAMPLE 11

In Example 4, the perfluoropolyether compound [XVIa] obtained in Reference Example 8 was used in place of the acid fluoride compound [XIIIa], and the trickling rate was changed to 1.0 g/min., the temperature of the preheated vaporization chamber to 220° C., the helium gas flow rate to 50 ml/min., and the reactor tube temperature to 330° C. As a result of the reaction, 202 g of the product was obtained in the dry ice-methanol trap and had the same analytical result as in Example 4.

EXAMPLE 12

In Example 11, the acid fluoride compound [XIIIc] obtained in Reference Example 9 was used in place of the perfluoropolyether compound [XVIa]. As a result of the reaction, 207 g of the product was obtained in the dry ice-methanol trap and had the same analytical result as in Example 4.

EXAMPLE 13

In Example 4, the acid fluoride compound [XIIId] obtained in Reference Example 10 was used in place of the acid fluoride compound [XIIIa], and 209 g of the product was obtained in the dry ice-methanol trap and 41 g of the product was obtained in the liquefied nitrogen trap.

Gas chromatography of total of the products obtained in both traps:

| | |
|---|---|
| $CF_3COF$ | 91.1% |
| $COF_2$ | 8.9% |

EXAMPLE 14

In Example 4, the n=1 fraction of the acid fluoride compound [XIIIe] obtained in Reference Example 11 was used in place of the acid fluoride compound [XIIIa] and 630 g of the n=1 fraction was trickled at a trickling rate of about 2.1 g/min. for about 5 hours.

Among the products trapped through the successive traps, 578 g of a colorless, transparent liquid product (gas at the ordinary temperature) was obtained in the dry ice-methanol trap (yield: about 92%).

The main component of the liquid product was identified by gas chromatography, infrared absorption spectrum analysis and F-NMR spectrum analysis to be perfluoropropionyl fluoride.

| Gas chromatography: | |
|---|---|
| $CF_3CF_2COF$ | 92.4% |
| $CF_3COF$ | 4.2% |
| $COF_2$ | 3.3% |

EXAMPLE 15

In Example 14, the n=2 fraction of the acid fluoride compound [XIIIe] obtained in Reference Example 11 was used in place of the the n=1 fraction of the acid fluoride compound [XIIIe] and 870 g of the n=2 fraction was trickled at a trickling rate of about 2.9 g/min. for about 5 hours. 783 g of the product was obtained in the dry ice-methanol trap (yield: about 90%), and the main component thereof was found to be perfluoropropionyl fluoride.

| Gas chromatography: | |
|---|---|
| $CF_3CF_2COF$ | 90.1% |
| $CF_3COF$ | 5.5% |
| $COF_2$ | 4.2% |

REFERENCE COMPARATIVE EXAMPLE

In Example 14, the n=0 fraction was used in place of the n=1 fraction of the acid fluoride compound [XIIIe], and the resulting product was also found to be perfluoropropionyl fluoride.

What is claimed is:

1. A process for producing a carbonyl fluoride compound represented by the following general formula [I]:

$$XCOF \qquad [I]$$

wherein X is a fluorine atom or $-CF_3$, which comprises thermally decomposing a polyether compound represented by the following general formula [II] at a temperature of about 180°–about 400° C. in the presence of an activated carbon catalyst:

$$RfO(CF_2CF_2O)_a(CF_2O)_b(O)_cRf' \qquad [II]$$

wherein Rf is a perfluoro-lower alkyl group; Rf' is $-COF$ or $-CF_3$; the $CF_2CF_2O$ groups, the $CF_2O$ groups and the O groups are distributed at random; a and b are other than 0, c can be zero and a+b+c is a value of not more than about 200.

2. A process according to claim 1, wherein perfluoro-lower alkyl group as Rf has 1 to 5 carbon atoms.

3. A process according to claim 1, wherein a+b+c is not more than about 40 in the general formula [II].

4. A process for producing a carbonyl fluoride compound represented by the following general formula [XI]:

$$CF_2XCOF \qquad [XI]$$

wherein X is $-CF_3$ or a fluorine atom, which comprises thermally decomposing a polyether compound represented by the following general formula [XII] at a temperature of about 180°–about 400° C. in the presence of an activated carbon catalyst:

$$RfO(CFXCF_2O)_nCFX'Y \qquad [XII]$$

wherein Rf is a perfluoro-lower alkyl group; X has the same meaning as defined above; X' is $-CF_3$, a fluorine atom or a hydrogen atom; Y is $-COF$, $-COOH$, $-COOR$ or $-CF_3$; R is a lower alkyl group; and n is 1–50.

5. A process according to claim 4, wherein the perfluoro-lower alkyl group as Rf has 1 to 5 carbon atoms.

6. A process according to claim 4, wherein n is 1–10 in the general formula [XII].

* * * * *